(12) United States Patent
Chang et al.

(10) Patent No.: US 11,385,224 B2
(45) Date of Patent: Jul. 12, 2022

(54) MAGNETIC SHIELDING FOR IVD AUTOMATION SYSTEM

(71) Applicant: Siemens Healthcare Diagnostics Inc., Tarrytown, NY (US)

(72) Inventors: Kung-Le Chang, Madison, NJ (US); Manuel Lavin, Mine Hill, NJ (US); Baris Yagci, Montclair, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 757 days.

(21) Appl. No.: 16/319,256

(22) PCT Filed: Jul. 19, 2017

(86) PCT No.: PCT/US2017/042922
§ 371 (c)(1),
(2) Date: Jan. 18, 2019

(87) PCT Pub. No.: WO2018/017755
PCT Pub. Date: Jan. 25, 2018

(65) Prior Publication Data
US 2019/0277839 A1    Sep. 12, 2019

Related U.S. Application Data

(60) Provisional application No. 62/365,256, filed on Jul. 21, 2016.

(51) Int. Cl.
*G01N 35/04* (2006.01)
*G01R 33/30* (2006.01)
(Continued)

(52) U.S. Cl.
CPC ....... *G01N 33/54326* (2013.01); *G01N 35/00* (2013.01); *G01N 35/04* (2013.01);
(Continued)

(58) Field of Classification Search
CPC .. G01N 33/54326; G01N 35/00; G01N 35/04; G01N 2035/00306; G01N 2035/046; G01R 33/30
See application file for complete search history.

(56) References Cited

U.S. PATENT DOCUMENTS 5,006,934 A    4/1991  Hashimoto et al.
5,770,461 A *  6/1998  Sakazume ............... B03C 1/288
                                                    436/526

(Continued)

FOREIGN PATENT DOCUMENTS

CN    101627308 A    1/2010
CN    102149892 A    8/2011
(Continued)

OTHER PUBLICATIONS

PCT International Search Report and Written Opinion dated Nov. 8, 2017 (11 Pages).

(Continued)

*Primary Examiner* — Jill A Warden
*Assistant Examiner* — John McGuirk

(57) ABSTRACT

Systems and methods for use in an in vitro diagnostics setting incorporating magnetic shielding to reduce exposure of any of samples, reactants, devices or people from exposure or prolonged exposure to magnetic or electromagnetic fields generated with the system. Some embodiments provide an automation system for use in an in vitro diagnostics setting comprising an automation track having a sidewall provided with magnetic shielding. In some embodiments, the magnetic shielding comprises an 80% nickel alloy.

5 Claims, 4 Drawing Sheets

(51) Int. Cl.
  *G01N 35/00* (2006.01)
  *G01N 33/543* (2006.01)

(52) U.S. Cl.
  CPC ... *G01R 33/30* (2013.01); *G01N 2035/00306* (2013.01); *G01N 2035/046* (2013.01)

(56) References Cited

U.S. PATENT DOCUMENTS

| | | | |
|---|---|---|---|
| 6,933,677 B1 * | 8/2005 | Karpen | H05K 9/0049 |
| | | | 315/85 |
| 2002/0153255 A1 | 10/2002 | Dinan et al. | |
| 2005/0115352 A1 | 6/2005 | Tanaka | |
| 2008/0290869 A1 | 11/2008 | Hutton et al. | |
| 2014/0373747 A1 | 12/2014 | Yagci et al. | |
| 2015/0226760 A1 * | 8/2015 | Itoh | B65G 35/066 |
| | | | 198/657 |
| 2016/0195526 A1 | 7/2016 | Venkatesan et al. | |
| 2017/0131310 A1 * | 5/2017 | Volz | G01N 35/04 |

FOREIGN PATENT DOCUMENTS

| | | | |
|---|---|---|---|
| CN | 102326087 A | 1/2012 | |
| CN | 103379812 A | 10/2013 | |
| CN | 104833814 A | 8/2015 | |
| EP | 2 908 138 A1 | 8/2015 | |
| JP | S56-076051 A | 6/1981 | |
| JP | H01196959 A | 8/1989 | |
| JP | H11-096959 A | 4/1999 | |
| JP | 2010-518403 A | 5/2010 | |
| JP | 2010-190811 A | 9/2010 | |
| JP | 2015-518187 A | 6/2015 | |
| JP | 2015-121438 A | 7/2015 | |
| WO | 2004/070391 A1 | 8/2004 | |
| WO | 2008/098236 A2 | 8/2008 | |
| WO | WO-2013064662 A1 * | 5/2013 | ............. B65G 54/02 |
| WO | 2013/116651 A1 | 8/2013 | |
| WO | 2016/012517 A1 | 1/2016 | |

OTHER PUBLICATIONS

Supplementary EP Search Report dated Jul. 8, 2019 of corresponding European Application No. 17831821.8, 5 Pages.
Calibration—Theory and Practice by Fluck Corporation, Jan. 31, 2000, pp. 335-338 of Chapter 7, ISBN 7-5026-1224-6.
English translation of Chinese Office Action of corresponding Chinese patent Application No. 201780045109.9 15 Pages.

\* cited by examiner

MAGNETIC SHIELDING FOR IVD AUTOMATION SYSTEM

CROSS-REFERENCE TO RELATED APPLICATIONS

This application claims the benefit of U.S. Provisional Application Ser. No. 62/365,256 filed Jul. 21, 2016, which is incorporated herein by reference in its entirety.

TECHNOLOGY FIELD

The present invention relates in general to magnetic shielding for use in an automation system for use in a laboratory environment and, more particularly to shielding systems for assisting in the transport and interaction with patient samples and/or reagents for in vitro diagnostics in a clinical analyzer.

BACKGROUND

In vitro diagnostics (IVD) allow labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from sample vessels and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer, which may include immunoassay (IA) and clinical chemistry (CC) stations.

An automation system for use with analyzers in an IVD environment moves tubes containing sample specimens between different stations within an analyzer or between analyzers. One method of transporting sample and reagent tubes is on a carrier, or vessel mover (VM) moved about via a magnetic track system. Such a system involves permanent magnets as well as complex electromagnets which operate to facilitate movement of the vehicle mover about the track as desired. As such, both reagent tubes and samples tubes are exposed to strong magnetic forces, as are reactants and other chemicals in the modules of the track services.

Thus, there is a need to protect the samples and/or reagents carried on the vessel movers (VM) and within the modules from the strong magnetic forces.

SUMMARY

Some embodiments provide an automation system for use in an in vitro diagnostics setting comprising an automation track having a sidewall provided with magnetic shielding. In some embodiments, the magnetic shielding comprises an 80% nickel alloy foil. In some embodiments, the magnetic shielding comprises an 80% nickel alloy coating or paint.

Some embodiments further comprise at least one vessel mover comprising a vessel holding area and a permanent magnet separated by magnetic shielding. In some embodiments, the magnetic shielding separating the vessel holding area and permanent magnet is 80% nickel alloy of thickness sufficient to reduce the magnetic field in the vessel holding area.

Some embodiments provide a cover for an in vitro diagnostic system module, the cover comprising at least one sidewall provided with magnetic shielding. In some embodiments, the magnetic shielding is applied to one or more of an internal surface, an external surface, or integrated within the at least one sidewall of the cover.

Some embodiments provide an in vitro diagnostic system with magnetic-based vessel mover system comprising magnetic shielding to reduce the amount of electromagnetic field exposure to reagents or chemical component within the system and/or devices and organisms outside the system. Some embodiments provide magnetic shielding on one or more surfaces between a magnetic or electromagnetic source in the magnetic-based vessel mover and an object to be protected. In some embodiments, the object to be protected is one or more of a reactant vessel, a sample vessel, a reaction chamber, an external device, or an organism.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

Figure 1:
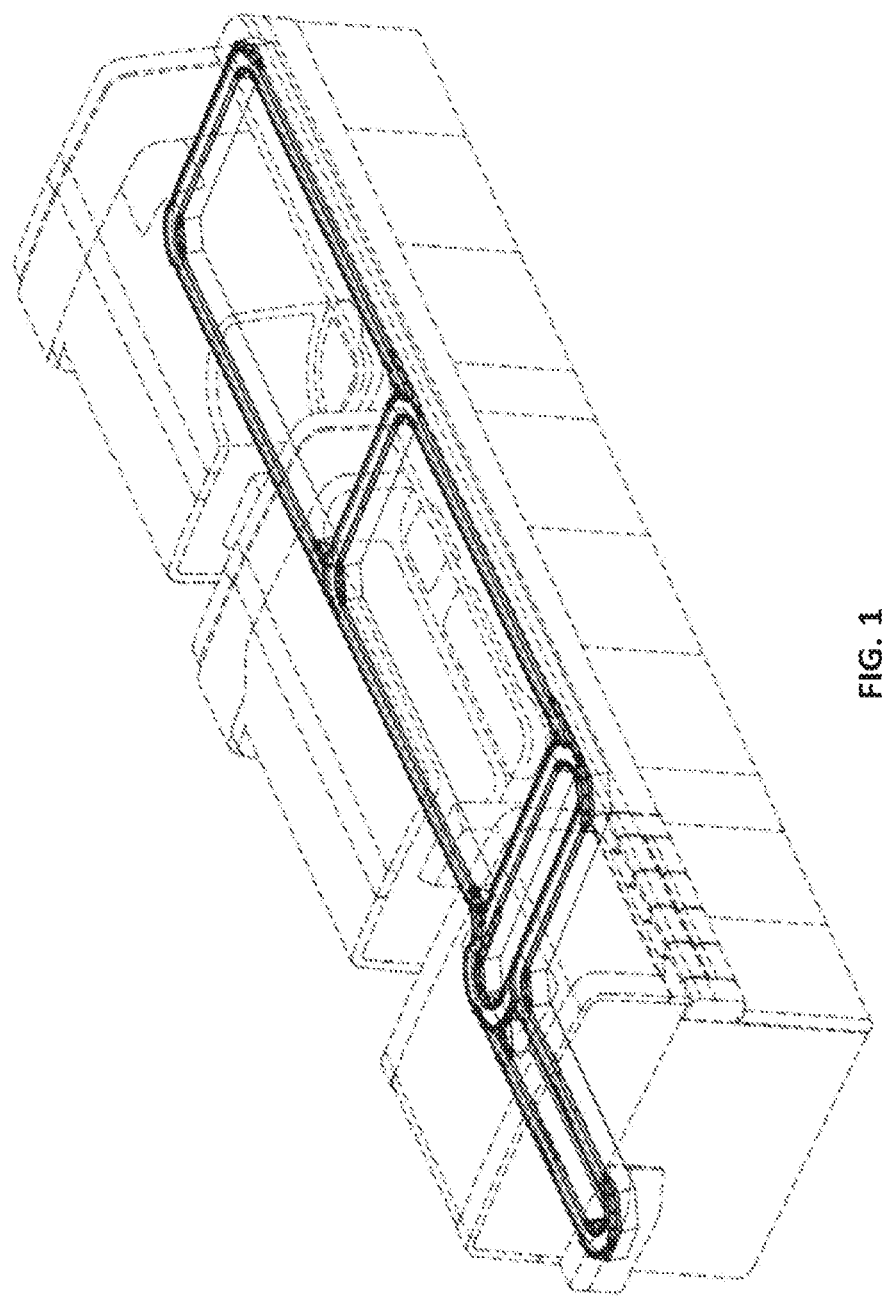
FIG. 1 depicts an exemplary IVD system employing a magnetic vessel moving system.

FIG. 1 depicts an exemplary IVD system employing a magnetic vessel moving system. This particular arrangement shows three modules, a sample handler, a clinical chemistry module, and immunoassay module, each having a cover, shown in dashed lines. The track of the magnetic vessel moving system is shown as making several loops which essentially surround the working parts of the instruments (which are omitted for clarity).

When using a laboratory automation system employing a magnetic track system, the samples and/or reagents on the vessel mover and/or within the analyzer or other modules are exposed to electromagnetic fields generated by the permanent and electromagnets employed in the track system. These magnetic forces may be strong enough to affect the performance of a particular analyzer, module, uptake system, or even with outside systems such as pacemakers and cellphones of the system operator. In worst case scenarios, the magnetic field may be up to 2000-5000 Gauss.

Sample or reagent exposure to this magnetic field may cause undesirable agglutination of particles within a sample or a reagent while on the vessel mover or within a module, may cause undesirable changes in concentration in the sample vessel and/or a reagent vessel, and/or may affect the sample and/or reagent in the analyzer itself. To minimize this effect, magnetic shielding can be employed in one or more locations throughout the IVD system.

Any location between the magnetic source and the area to be protected is a candidate for magnetic shielding. Suggested locations for shielding are noted in the drawing figures with an S. These locations are suggestions, and are not meant to be the only locations suitable for shielding. For example, and not limited, magnetic shielding may be employed in the vessel mover below the sample and/or reagent vessels, in the vessel mover walls, in instrument panels, to covers in the IVD that protect access to the vessel mover, and other locations. Locations where samples or reagents are aspirated or loaded are particularly good candidates for magnetic shielding, as there is some thought that samples and reagents in this state are more subject to magnetic fields.

Figure 2:
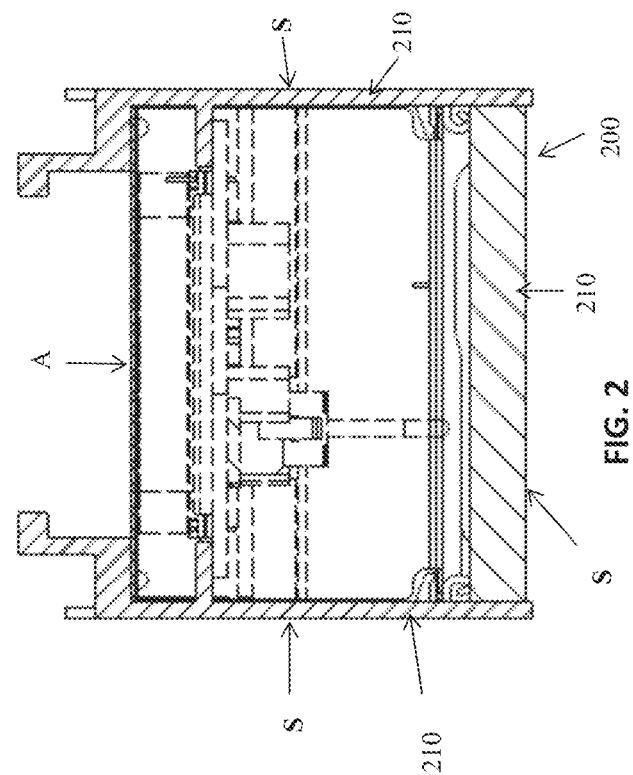
FIG. 2 is a cross-sectional view of a typical section of track in a magnetic vessel mover system.

FIG. 2 is a cross-sectional view of a typical section of track 200 in a magnetic vessel mover system. The horizontal surface A can be, for example, a stainless steel plate that facilitates electromagnetic interaction between, for example, a permanent magnet in the base of a vessel mover (e.g. puck; not shown) and the electromagnetic field generator(s) found in the track section below the horizontal surface. In use, the electromagnetic field generators below the track surface generate strong magnetic fields to facilitate movement of the vessel mover or vessel movers, multiple sections of track may or may not emit an electromagnetic field at a given time. The horizontal surface A must be suitable for passing the electromagnetic field to facilitate movement of the vessel mover, and may be made from stainless steel or other suitable material. Typically, the sidewalls 210 of the track are made from extruded aluminum because it is light weight, low cost, and non-magnetic. Aluminum has minimal magnetic shielding effect. Thus, any sample, reagent, or device (e.g. pacemaker, cell phone) nearby could be affected by the magnetic fields emitted during use. Thus, the sidewalls 210 on their exterior or interior surfaces may be provided with electromagnetic shielding material. This will minimize the "leakage" of electromagnetic field outside the track. Similarly, the upper and sidewalls of the base of the vessel mover (see FIG. 3 and discussion below) could also be provided with magnetic shielding to reduce the exposure of the samples and/or reagent carried thereupon.

Figure 3:
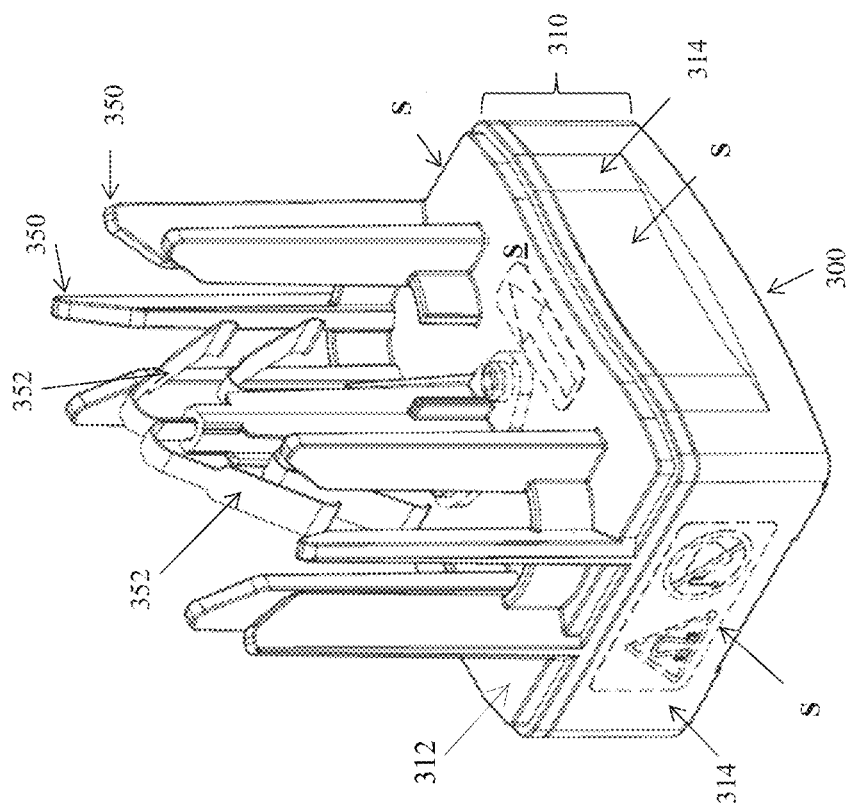
FIG. 3 shows an exemplary vessel mover suitable for use in a IVD system. As shown, the vessel mover includes a base portion which may include materials for interacting with a magnetic transportation system, which allows and facilitates movement of the vessel mover on a track.

FIG. 3 shows an exemplary vessel mover 300 suitable for use in an IVD system. As shown, the vessel mover 300 includes a base portion 310 which may include materials for interacting with a magnetic transportation system, which allows and facilitates movement of the vessel mover on a track. In some embodiments, the base 310 houses a permanent magnet. The base 310 has an upper wall 312 above which, various tube position and capture guides 350 and springs 352 are found for positioning sample and/or reagent tubes. The upper wall 312 of the vessel mover 300 is an ideal location for magnetic shielding. By placing magnetic shielding along this upper wall 312, the shielding is located between the magnetic source and the sample and/or reagent. Additional shielding can be placed along or within the sidewalls 314 of the vessel mover base. As noted previously, the magnetic shielding can be a foil, coating, or paint containing magnetic shielding material, such as but not limited to 80% nickel alloy. The magnetic shielding may be located on any or all of the interior surface of the vessel mover walls, the exterior surface of the vessel mover walls, and/or internally within the vessel mover walls. In some embodiments, the walls themselves could be made from the magnetic shielding material.

Figure 4:
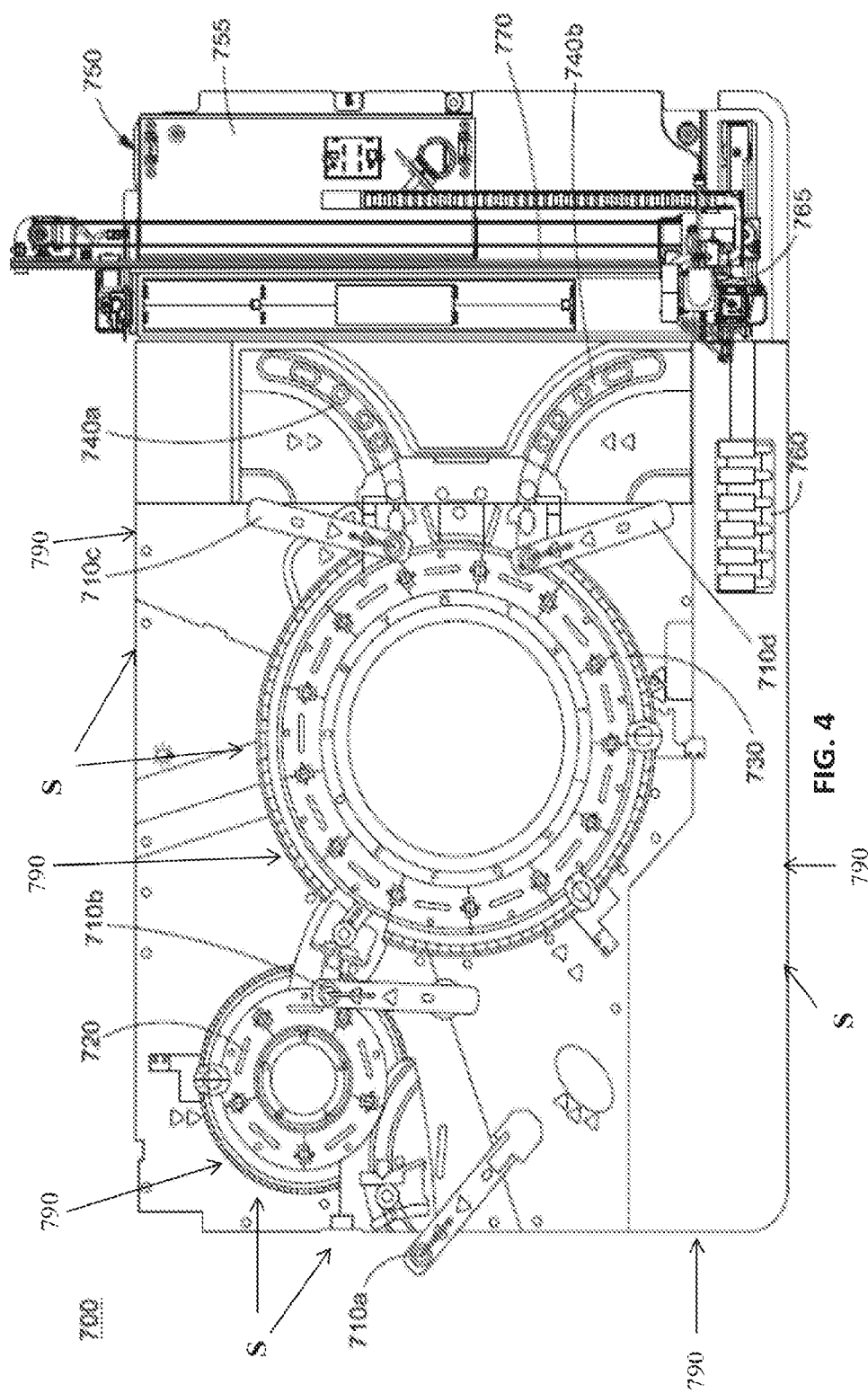
FIG. 4 shows an exemplary analyzer module.

The instruments or analyzers of an IVD system are typically arranged within a loop or multiple loops of track, potentially creating prolonged exposure of any reagent or chemical housed within the analyzer to electromagnetic fields. In some instances, these reagents or chemicals are housed in a reagent compartment (e.g. a reagent carousel). FIG. 4 depicts a plan view of an exemplary analyzer module 700. The outer boundaries shown generally represent an internal boundary of the track (not shown). Magnetic shielding provided either on the outer boundary of the analyzer module or the inner boundary of the track would protect the instruments, reagents, and samples within the analyzer module. Within the analyzer are multiple substructures, such as a sampling arm 710a, a dilution carousel 720, a reaction ring 730, and a reactant carousel (not shown, as obscured). These compartments house vessels containing samples, reactants, or active reactions. By applying magnetic shielding to the sidewalls 790 of such compartments, or even to the vessels themselves, these vital reagent or other chemicals can be protected from prolonged exposure to electromagnetic fields produced by the nearby track system. Depending upon the application, such shielding can also prevent undesirable changes in concentration that may occur if a reagent were to contain magnetic particles that could be affected by the magnetic field.

Figure 5:
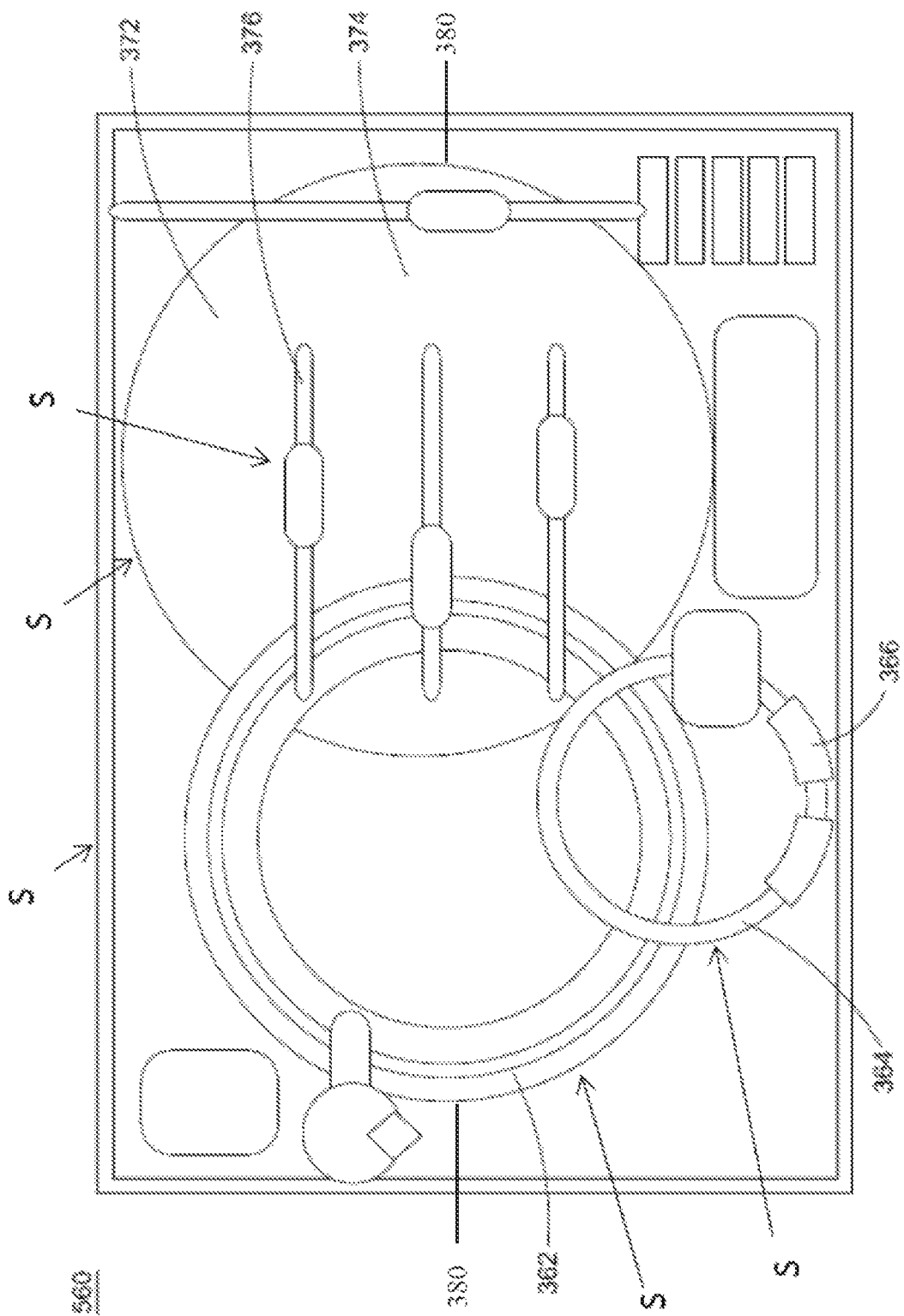
FIG. 5 shows another exemplary analyzer module.

FIG. 5 shows a schematic of an immunoassay analyzer module 560 that can be employed in an IVD system. Immunoassay analyzer module 560 is a clinical analyzer that automates heterogeneous immunoassays using magnetic separation and chemiluminescence readout. The precise arrangement and parts of the immunoassay module are detailed in other applications, but importantly, includes a reagent compartment 372, a reagent autoloader 374, reagent probes 376, and incubation rings 362. Any one of these areas or combination of areas can be protected by the magnetic shielding as contemplated herein. For example, the perimeter sidewalls 380 of the reagent compartment 372 can be provided with magnetic shielding to protect the reagents housed therein. Similarly, the sidewalls 380 of the incubation rings 362 can be so protected. The area of the reagent probes can also be protected. These areas have been designated with an S depicting areas or surfaces where shielding may be applied.

Regardless of the instrument or instrument module, reagents are particularly susceptible to the effects of both electro- and permanent magnets during the aspiration or loading operations. Areas involving loading or aspiration, therefore, may be protected by magnetic shielding.

In practice, the various modules and analyzers are provided with covers, typically made from plastic, to protect the samples and the instrument itself. As described above, the area of the instrument and near the track can be subject to intense electromagnetic fields. The covers themselves could be covered, coated, impregnated, or otherwise provided with magnetic shielding to minimize external exposure to the magnetic fields produced by the track system. In FIG. 1, the covers are depicted in dotted lines, while the underlying magnetic track is shown in solid lines. The analytical instrumentation, itself, has been omitted for clarity. By placing shielding in the cover, unwanted effects are minimized on external devices such as computers, pacemakers, cell phones, etc. or people.

Although any magnetic shielding will suffice nickel alloy may be used. An 80% nickel alloy foil is particularly well-suited for the task, because it is light weight, can be customized in size, shape, configuration, and thickness as needed. Nickel foil shielding material can be applied in specific areas of concern, or could be applied uniformly throughout the system (for example, in the instrument panels.) The thickness of the magnetic shielding is determined by the material and the amount of shielding it yields and is desired. Thickness may range from a few microns to several millimeters or more. In some examples, the thickness is 1 micron, 10 microns, 100 microns, 500 micron, 1 millimeter, 5 millimeters, or any range of values therebetween. In instances where the magnetic shielding is embedded in another material, such as paint or plastic, the magnetic shielding material is present in an amount effective to have the shielding effect.

Alternatively, a magnetic shielding (such as 80% nickel alloy) could be formulated into a coating or paint which could be applied to the parts of the vessel mover, the track sidewalls, instrument panels, or other parts of the IVD system. Such a coating or paint benefits from ease of application, uniformity, ability to build up thicknesses, and other effects.

Importantly, although 80% nickel alloys offer appropriate levels of magnetic shielding, other percentages may be employed. For example, about 50% to about 90% nickel may be employed. Some embodiments of the nickel alloy magnetic shielding material comprise about 50% nickel, about 60% nickel, about 70% nickel, about 80% nickel, or about 90% nickel.

Other suitable types of magnetic shielding could be employed. Magnetic shielding materials include but are not limited to sheet metal, metal screen, metal foam, and other forms. Suitable metals for magnetic shielding including nickel, copper, alloys thereof, and other metals.

It is noted that magnetic shielding contemplated herein need not be, and likely does not achieve 100% blockage of the magnetic field. Rather, the field can be reduced or redirected away from the area in question.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations that fall within the true spirit and scope of the invention.

We claim:

1. An automation system for use in an in vitro diagnostics (IVD) setting comprising:
    an automation track defined by at least two sidewalls and a horizontal surface extending therebetween,
    wherein the at least two sidewalls define interior and exterior surfaces, and magnetic shielding material is provided at one or more of the interior surface, the exterior surface, or integrated within the sidewalls themselves, and
    wherein the horizontal surface is devoid of magnetic shielding material.

2. The automation system of claim 1, wherein the magnetic shielding material comprises an 80% nickel alloy foil applied to at least one of the interior surfaces or exterior surfaces of the sidewalls.

3. The automation system of claim 1, wherein the magnetic shielding material comprises an 80% nickel alloy coating applied to at least one of the interior surfaces or exterior surfaces of the sidewalls.

4. The automation system of claim 1, further comprising at least one vessel mover comprising a vessel holding area and a permanent magnet separated by magnetic shielding material.

5. The automation system of claim 4, wherein the magnetic shielding material separating the vessel holding area and permanent magnet is an 80% nickel alloy of thickness sufficient to reduce the magnetic field in the vessel holding area.

* * * * *